United States Patent [19]

Nordling

[11] 4,261,365
[45] Apr. 14, 1981

[54] DEMAND-TYPE CARDIAC PACER HAVING DYNAMIC IMPEDANCE SWITCH

[75] Inventor: Neal F. Nordling, White Bear Lake, Minn.

[73] Assignee: Cardiac Pacemakers, Inc., St. Paul, Minn.

[21] Appl. No.: 44,769

[22] Filed: Jun. 1, 1979

[51] Int. Cl.³ .............................................. A61N 1/36
[52] U.S. Cl. ............................................. 128/419 PG
[58] Field of Search .................. 128/419 PG, 419 PT

[56] References Cited

U.S. PATENT DOCUMENTS

| | | | |
|---|---|---|---|
| 3,835,865 | 9/1974 | Bowers | 128/419 PG |
| 4,041,953 | 8/1977 | Anderson et al. | 128/419 PG |
| 4,114,627 | 9/1978 | Lewyn et al. | 128/419 PG |
| 4,170,999 | 10/1979 | Allen et al. | 128/419 PG |

*Primary Examiner*—William E. Kamm
*Attorney, Agent, or Firm*—Orrin M. Haugen; Thomas J. Nikolai

[57] ABSTRACT

An improvement in a demand-type heart pace system in which the normally high input impedance of the R-wave sensing amplifier is reduced for a predetermined time interval following the generation of a heart stimulating impulse such that the charge on the pulse generator's voltage doubling capacitor following the generation of the stimulating impulse may more rapidly be restored to thereby prevent false detection of naturally occurring R-waves. Following the predetermined time interval, the input impedance of the R-wave amplifier is again returned to a high value in anticipation of the receipt of a natural R-wave signal following the completion of a refractory period. Digital logic circuitry is utilized for controlling the conduction state of semiconductor switches which are connected in parallel with the resistors normally establishing the amplifier's input impedance and the recharge path for the voltage doubling capacitor.

3 Claims, 4 Drawing Figures

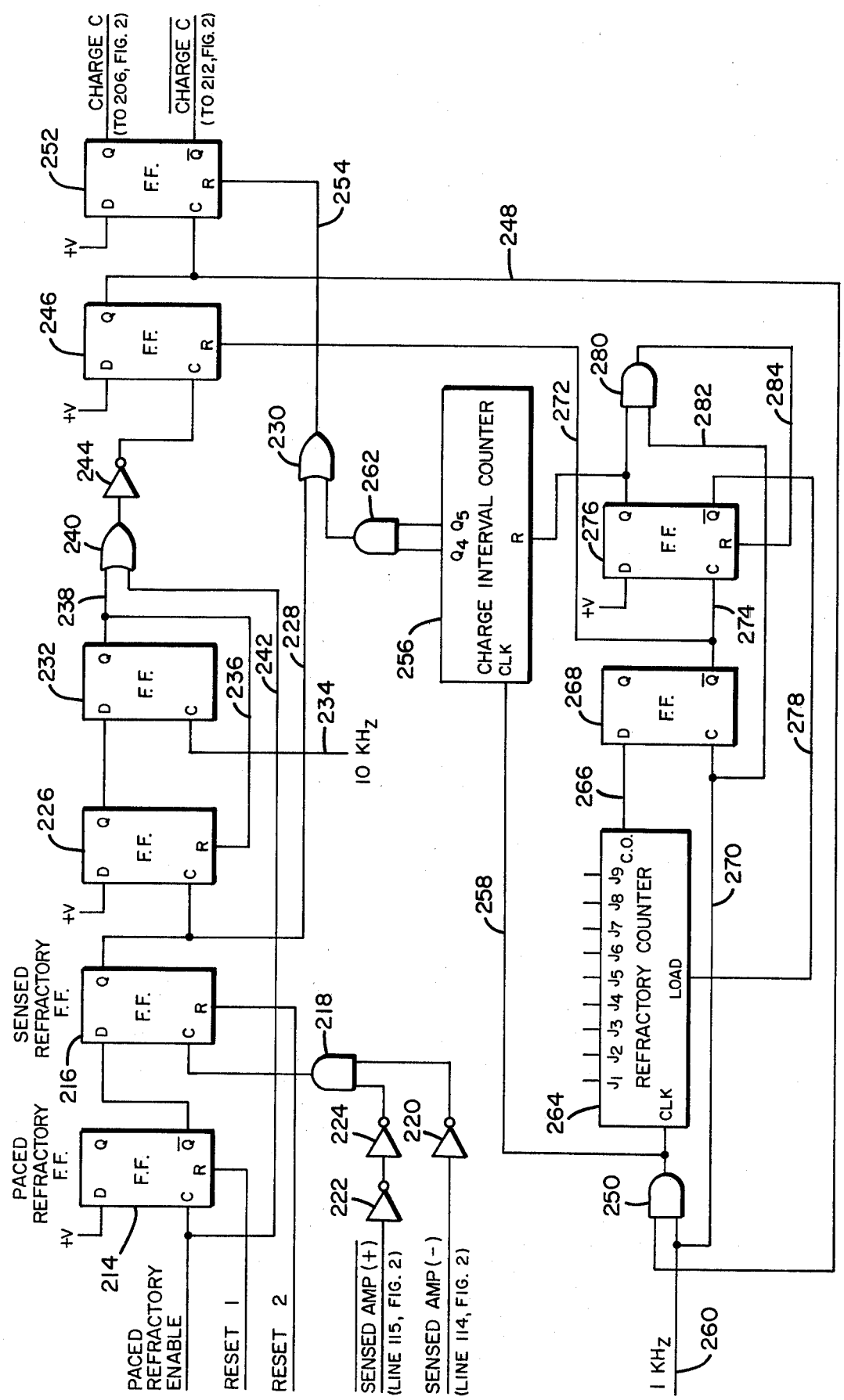

DEMAND-TYPE CARDIAC PACER HAVING DYNAMIC IMPEDANCE SWITCH

BACKGROUND OF THE INVENTION

I. Field of the Invention

This invention relates generally to an arrangement for selectively altering the input impedance of an operational amplifier, and more specifically to the adaptation of this approach to the operational amplifier employed in a demand-type pacemaker such that the system functions in a more reliable manner.

II. Discussion of the Prior Art

In the now abandoned application of David J. Fischer, Ser. No. 880,895, filed Feb. 24, 1978 and assigned to the assignee of the instant application, there is described a digital, programmable demand-type cardiac pacer system in which a pulse generator is adapted to be coupled by way of a catheter lead arrangement to the heart of the patient. As with all demand-type units, in the absence of naturally occurring heartbeat activity, the system functions to generate pulses at a desired rate for application to the heart of the patient. The same electrodes which are utilized to apply artificial stimulating pulses to the heart in the absence of naturally occurring heart activity are also used to pick up the electrical signals generated upon depolarization of the heart muscle and apply these signals to the R-wave sensing amplifier, the output of which is used to inhibit or reset the pulse generator so that it does not produce artificial stimulating pulses when normal R-waves are being produced on a regular basis. It is to be further noted that the system of the Fischer application includes a relatively large capacitor (the voltage doubling capacitor) in circuit with the pacer leads and, therefore, with the input of the R-wave sensing amplifier.

To achieve a desired gain from the operational amplifier, it is imperative that the input impedance of the amplifier be relatively high. In fact, the American Association for Medical Instrumentation (AAMI) has an established standard requiring an input impedance for a sensing amplifier used in the amplification of signals occurring upon the depolarization of body cells of at least 20 thousand ohms. It is found that the time constant of the input circuit to the R-wave sensing amplifier is quite large in that it is the product of the input impedance of the amplifier and the capacitance of the voltage doubling capacitor which determine that time constant.

When an artificial stimulating pulse is produced by the pulse generator and applied to the heart by way of the heart contacting electrodes, this large time constant may prevent sufficiently rapid recovery of the over-shoot appearing at the trailing edge of the applied impulse. If the time interval required for the over-shoot voltage to return to the normal base level is too long, it may exceed the refractory period of the system. As a result, the potential difference appearing across the input of the sensing amplifier at the completion of the refractory period may be sufficiently large to be interpreted by the system as an R-wave. When this happens, the system is deceived into believing that the heart is producing R-waves, thereby inhibiting, temporarily, the generation of artificial stimulating impulses. Thus, a patient suffering complete heart block would not be receiving the artificial stimulating impulses required for proper pacing.

OBJECTS

It is accordingly the principal object of the present invention to provide an improvement for a demand-type cardiac pacer device.

Another object of the invention is to provide a means whereby the input impedance of a R-wave sensing amplifier may be maintained at a relatively high level at the time that it is to function in a sensing mode, while still maintaining a relatively low time constant characteristic at its input circuit for a predetermined time following the receipt of an artificial stimulating impulse from the pacer pulse generator.

A further object of the invention is to provide a means whereby the performance of a demand-type cardiac pacer circuit can be rendered more reliable.

SUMMARY OF THE INVENTION

The foregoing objects and advantages are attained through the use of a dynamic impedance switch which is operative to reduce the input impedance of a sense amplifier for a predetermined period following the occurrence of an artificial stimulating pulse such that the time constant is thereby made sufficiently short so that there is a very small residual DC charge at the electrode site at the time that the refractory period expires. Hence, the input amplifier is not led to believe that a R-wave is present at its input.

In carrying out the invention, semiconductor switches are connected in parallel with the resistor elements defining the input impedance of the operational amplifier. These switches are normally in a non-conducting condition and thereby do not materially affect the magnitude of the input resistance. However, at the trailing edge of an output from the pacer pulse generator, the semiconductor switches are turned on thereby dropping the input resistance significantly, the switches remaining conductive for a predetermined time interval sufficiently long to permit the voltage doubling capacitor to recover but less than the normal refractory period for the pulse generator. As such, any residual charge remaining at the amplifier inputs at the conclusion of the refractory period is too low to be interpreted by the sense amplifier as an input R-wave. Because only the timing of the pacer output pulse and not its biphasic symmetry is altered by the present invention, its use does not result in electrolysis or polarization at the electrode attachment site, which, of course, is highly advantageous.

Further features and advantages of the invention will become apparent to those skilled in the art from the following detailed description of a preferred embodiment when considered in conjunction with the accompanying drawings in which like numerals in the several views refer to corresponding parts.

DESCRIPTION OF THE DRAWINGS

FIG. 3 is a logic diagram of a control circuit used to control the on-time of the dynamic impedance switch.

DESCRIPTION OF THE PREFERRED EMBODIMENT

Figure 1:
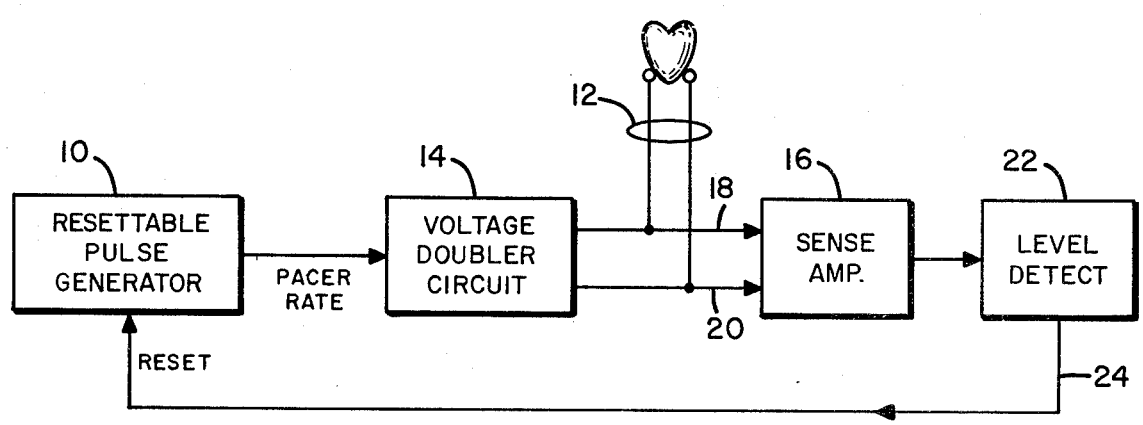
FIG. 1 is a system block diagram.

Referring first to FIG. 1, there is shown a simplified block diagram of a typical demand-type cardiac pacer circuit with which the present invention finds use. Indicated by numeral 10 is a resettable pulse generator which is arranged to produce output trigger pulses termed "pacer rate pulses", at a prescribed rate unless the pulse generator is reset through the occurrence and detection of a heart depolarizing signal picked up by the implanted electrodes 12. The output from the resettable pulse generator is applied to a voltage doubler circuit 14 which, when triggered by the pacer rate pulses serves to apply a potential substantially equal to twice battery voltage to the heart of the patient by way of the same heart contacting electrodes 12. The manner in which the resettable pulse generator 10 is reset involves the use of a sense amplifier 16 whose input terminals 18 and 20 are connected to the proximal end of the leads or electrodes 12 and, as such, serves to amplify the low level electrical signal R-wave produced upon depolarization of the cells comprising the heart muscle. The amplified R-wave signal is applied to a level detect circuit 22 and, provided the output from the sense amplifier exceeds predetermined threshold values, the level detector outputs a reset pulse on line 24 which may then reset the pulse generator 10, provided any refractory period, either a paced refractory period or a sensed refractory period, has expired.

Further details of the overall system operation can be discerned from a reading of the aforereferenced Fischer application.

Figure 2:
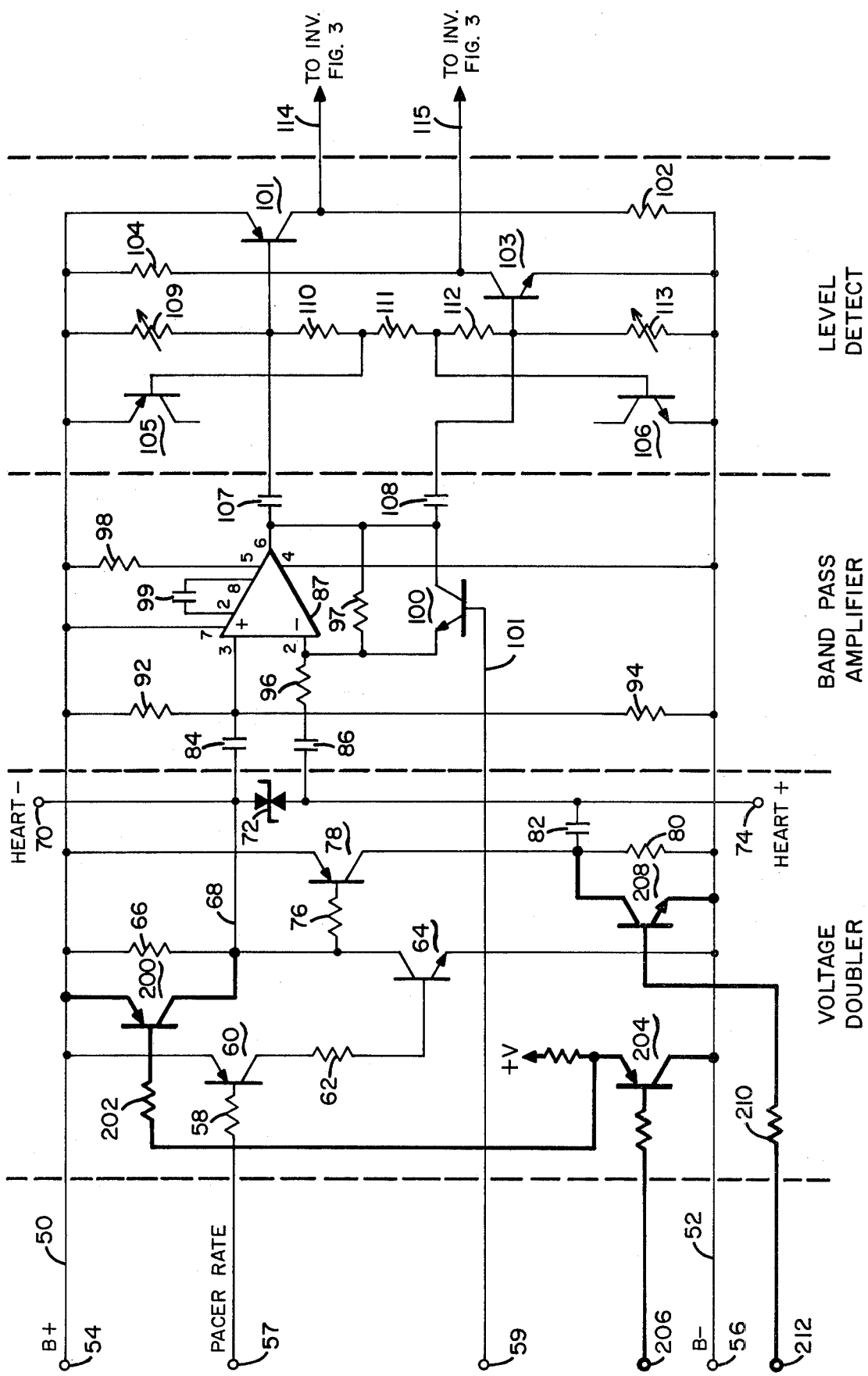
FIG. 2 is a schematic elecrical diagram of a portion of a typical demand-type pacemaker including the output electrodes, voltage doubler and R-wave sense amplifier.

Referring next to FIG. 2, there is shown an electrical schematic diagram of the voltage doubler portion, the bandpass amplifier portion and the level detect portion of a typical heart pacemaker system. In fact, the arrangement shown in FIG. 2 closely resembles that shown in FIG. 2 of the aforereferenced Fischer application and the description thereof is incorporated by reference herein. Hence, it is believed unnecessary to repeat that description, suffice it to say that the resistors 66 and 80 serve principally in establishing the input impedance of the operational amplifier 87 and that the capacitor 82 is the so-called voltage doubling capacitor employed for effectively doubling the amplitude of the voltage produced by the pulse generator before the signal is applied to the patient's heart by way of the leads (not shown) which are adapted to be connected to the terminal points 70 and 74 in FIG. 2.

Figure 4:
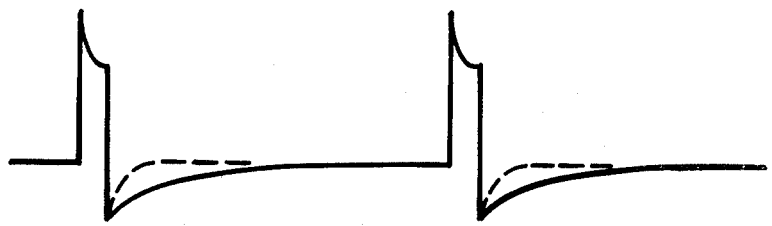
FIG. 4 illustrates by means of waveforms the principles of operation of the instant invention.

Ignoring for the moment the circuitry shown in heavy line representation in FIG. 2, upon receipt of a pacer rate signal at the input terminal 57, transistor 60 is turned on causing transistors 64 and 78 to also be rendered conductive. With transistor 78 conducting, a voltage substantially two times the battery supply is applied across the heart leads. That is, the voltage stored on the capacitor 82 is added to the supply voltage B+ and used to stimulate the heart muscle. At the trailing edge of the triggering pulse applied to the terminal 57, transistors 60, 64 and 78 are again switched off and the capacitor 82 begins to recover its charge by way of the path from the B+ terminal 54, resistor 66, conductor 68, diode 72, and the resistor 80 back to the negative bus terminal 56. The resulting waveform of the pacer pulse is illustrated by a solid line representation in FIG. 4.

Because of the large time constant of the circuit involving the resistors 66 and 80 and the voltage doubling capacitor 82, a significant potential remains across the input terminals of the operational amplifier 87 for a significant period of time. In fact, it is found that when an attempt is made to provide appreciable gain through the amplifier 87 by maintaining the input impedance thereto at a relatively high value, the time constant may exceed the refractory period established for the system and when this occurs, the residual overshoot potential from a preceding pacer pulse may be interpreted as a received R-wave, the net results being that the pacer circuit may be inhibited when, in fact, the heart is failing to produce spontaneous depolarization (R-wave) impulses.

To obviate this problem, there is provided a dynamic impedance switch which, with reference to FIG. 2, includes the circuitry represented in a heavy line presentation. Specifically, a semiconductor switch 200 has its emitter-to-collector path connected directly in parallel with the recharge resistor 66. Its control electrode is coupled through a resistor 202 to a further transistor switch 204 whose control input terminal 206 is adapted to be coupled to the timing control network of FIG. 2, all as will be further described hereinbelow. In a somewhat similar fashion a semiconductor switch 208 has its emitter to collector path connected in parallel with the recharge resistor 80 and the control electrode of the switch 208 is coupled through a resistor 210 to a terminal 212 which, too, is adapted to be connected to the timing control circuit of FIG. 3.

With no limitation intended, the semiconductor switch member 200 is illustrated as a PNP transistor while the switch 208 is illustrated as a complementary or NPN transistor. The transistor 204 being a PNP type, when a negative signal is applied to the input terminal 206, transistor 204 turns on causing a negative impulse to be applied to the control electrode of the transistor 200. If at the same time the timing circuit of FIG. 3 provides a positive input pulse at the terminal 212, the semiconductor switch 208 will be rendered conductive. With both transistors conducting, the impedance of the recharge path for the voltage doubling capacitor 82 drops to a relatively low value allowing a rapid recharging of the capacitor 82 as represented by the dashed line trace in FIG. 4. However, when the control signals applied to the terminals 206 and 212 switch to an opposite binary state, the transistors 200 and 208 will again be rendered non-conducting. Thus, the resistors 66 and 80 are again effectively switched back into the circuit. These resistors are of a sufficiently high value to ensure that the operational amplifier 87 will adequately amplify any R-wave signals which may be picked up by the pacer electrodes.

Referring now to FIG. 3, there is shown the timing and control circuitry used to control the conductivity of the semiconductor switches 200 and 208 so as to achieve synergistic operation of the heart stimulating and heart monitoring portions of the overall system. If the circuitry of FIG. 3 is compared to that illustrated on FIG. 6 of the aforereferenced Fischer application, the manner in which the prior art logic circuitry may be modified to incorporate the dynamic impedance switching feature of the present invention can readily be visualized. In the arrangement shown in FIG. 3, there is provided a Paced Refractory flip-flop 214 having its complementary output terminal ($\overline{Q}$) connected to the D-input terminal of the Sensed Refractory flip-flop 216.

Paced Refractory Enable signals (logic 1 during pacer pulse output) are adapted to be applied to the Clock input terminal of the Paced Refractory flip-flop 214, this enable signal being produced as described in the Fischer application. The Clock terminal of the Sensed Refractory flip-flop 216 receives its input from the output of the Level Detect circuitry of FIG. 1 by way of an AND gate 218. This last-mentioned gate is, in turn, coupled to the output lines 114 and 115 of FIG. 1 by way of inverter 220 and the chain including inverters 222 and 224 respectively.

The Q output of the D-type flip-flop 216 is connected to the Clock input terminal of a further D-type flip-flop 226 and by way of a conductor 228 to a first input of an OR gate 230. The Q output of the flip-flop 226 is, in turn, connected to the D-input terminal of a still further flip-flop 232 which is regularly clocked by input signals on the line 234 which connects to the 10 Khz. clock source used in the system of the Fischer application.

The Q output of the flip-flop 232 is connected back by a conductor 236 to the Reset terminal of the D-type flip-flop 226 and by way of a conductor 238 to a first input terminal of OR gate 240. The second input to OR gate 240 comes by way of conductor 242 and, as such, carries the "Paced Refractory Enable" signal. The output from OR circuit 240 is inverted in inverter circuit 244 and applied to the Clock input terminal of a flip-flop 246 whose Q output is connected by a conductor 248 as an enable signal for AND gate 250. This same output from the flip-flop 246 is connected to the Clock terminal of the Charge flip-flop 252 whose Q output connects to terminal 206 in FIG. 2 and whose $\overline{Q}$ output line connects to terminal 212 in FIG. 2.

The output from the OR gate 230 connects to the Reset terminal of the Charge flip-flop 252 by way of conductor 254 and, as such, the Charge flip-flop 252 is continuously reset so long as the Sensed Refractory flip-flop 216 is set.

The Charge flip-flop 252 will also be reset by a timing control circuit which includes the Charge Interval Counter 256. This counter is adapted to receive clock pulses by way of conductor 258 from the output of the AND gate 250 which receives regularly occurring clock pulses at, for example, a 1 KHz. rate by way of input line 260. As is illustrated in FIG. 3, the output lines from stages 4 and 5 of the Charge Interval Counter 256 are applied as inputs to an AND gate 262 whose output is connected as a second input to the aforementioned OR gate 230. Thus, when the contents of the counter reach 11000 (decimal 24) gate 262 will be enabled and the Charge flip-flop 252 will be reset. With a clock rate of 1 KHz., this corresponds to a time interval of 24 milliseconds.

The output from the gate 250 is also connected to the Clock input of a still further counter termed the Refractory Counter 264. This may be a ripple-down type counting device which is periodically preloaded with a desired initial value and which is decremented by 1 each time a clock pulse is received at its Clock input terminal. When the contents of the counter pass through 0, an output appears at the Carry Output terminal (CO) which is connected by a conductor 266 to the D-input of a D-flip-flop 268 which is arranged to be clocked by the 1 KHz. pulses applied to the line 260 by way of a conductor 270. The $\overline{Q}$ output of this last-mentioned flip-flop is connected by way of a conductor 272 to the reset input of the D-type flip-flop 246. It is further connected by a conductor 274 to the clock input terminal of a still further D-type flip-flop 276. The $\overline{Q}$ output of flip-flop 276 is connected to the Load terminal of the Refractory Counter 264 by way of conductor 278. Thus, when the output on this line is a binary high, the preload value intended for the counter 264 is entered therein. The Q output of flip-flop 276 is applied as an enable input to AND gate 280 whose second input receives the 1 KHz. clock pulses from the lines 260 and 270 by way of a conductor 282. The output of AND gate 280 is connected back by a conductor 284 to the reset input terminal of the D-type flip-flop 276.

Now that the details of the construction of the timing and control circuitry for the dynamic impedance switch have been set forth, consideration will be given to the manner in which this circuit operates to control the conductivity state of the semiconductor switches 200 and 208 in FIG. 2.

OPERATION

Referring then to FIG. 3, it is to be noted that the flip-flop 214 controls the "paced refractory period" while the flip-flop 216 controls the "sensed refractory period". As such, flip-flop 214 corresponds to flip-flop 502 in the system of the Fischer application while flip-flop 216 of FIG. 2 corresponds to the flip-flop 500 of FIG. 6 of the Fischer application. The flip-flop 246 controls the basic refractory period while the flip-flop 252 controls the charge cycle period. To begin with, both counters 256 and 264 are in a reset condition. Flip-flop 214 as well as all of the other flip-flops with the exception of flip-flop 268 are also assumed to be in a reset condition. Thus, when a pacer pulse occurs, it causes a positive going pulse to be impressed upon the Paced Refractory Enable line which then sets the Paced Refractory flip-flop 214. In that the complementary ($\overline{Q}$) output of the flip-flop 214 is connected to the D-terminal of the Sensed Refractory flip-flop 216, that flip-flop along with flip-flops 226 and 232 are inhibited from changing state until termination of the refractory period.

The Paced Refractory signal propagates through gate 240 and inverter 244 causing a negative going pulse at the Clock input terminal of the Refractory Control flip-flop 246. This transition clocks the Charge Control flip-flop 252 to its set condition, thus initiating the charge cycle. The outputs from the flip-flop 252 are coupled to the input terminals 206 and 212 of the semiconductor switch devices 200, 204 and 208 of FIG. 2 such that these switches are rendered conductive to thereby reduce the input impedance of the amplifier 87 to a low value and to reduce the resistance in the charging path for the voltage doubling capacitor 82 to a low value.

At the same time, the AND gate 250 is enabled, allowing the 1 KHz. clock pulses on the line 260 to propagate therethrough so as to be applied to the Clock input terminals of the Charge Interval Counter 256 and the Refractory Counter 264. Counter 256 is a conventional ripple-up counter which counts until both stages $Q_4$ and $Q_5$ thereof are set. As mentioned earlier, this corresponds to a binary digital value of 11000 or a 24 millisecond interval, assuming a 1 KHz clock. At this time, AND gate 262 is enabled causing a reset pulse to propagate through OR gate 230 and by way of conductor 254 to reset the charge control flip-flop 252, thereby terminating the Charge Cycle interval. At the termination of the Charge Cycle interval, the polarity of the signals applied to the terminals 206 and 212 of FIG. 2 is reversed, rendering the semiconductor switching devices 204, 200 and 208 non-conductive.

The Refractory Counter 264 is a presettable ripple-down counter which decrements with each clock pulse until it passes through 0. The counter 264 is intended to be initially loaded with a value corresponding to a desired refractory time interval and, as such, corresponds closely in function to the Refractory Interval Counter 526 illustrated in FIG. 6 of the Fischer application. When the carry output (CO) of counter 264 goes negative, the flip-flop 268 is momentarily switched to its set state and then reset on the next occurring clock pulse applied thereto by way of line 270. The momentary positive transition of the $\overline{Q}$ output of flip-flop 268 causes the flip-flop 246 to be reset which, in turn, inhibits AND gate 250, disabling the clock and furthermore, switches flip-flop 276 to its set conditon. The negative transition of the $\overline{Q}$ output of the flip-flop 276 causes the Refractory Interval Counter 264 to be preset with data defining the desired length of the refractory period as is specified by the J1 through J9 inputs. On the next succeeding clock pulse, however, the D-input to flip-flop 268 is again high, causing it to be reset at the next clock time and the AND gate 280 is thereby enabled, causing the flip-flop 276 to be reset by way of the pulse carried by line 284. In this fashion, all of the circuitry associated with the basic refractory period is now initialized for a succeeding refractory period.

It is also to be noted that the $\overline{Q}$ output of the flip-flop 268 activates the circuitry of the Fischer application to permit the refractory period to be extended in the presence of noise. The manner in which this is accomplished is fully set forth in the Fischer application and need not be repeated here in that it is not directly related to the circuitry associated with the dynamic impedance switching concept of the present invention. It is related, however, to the extent that following any extension of the refractory period precipitated by the presence of noise, the flip-flop 214 is reset in anticipation of the receipt of a subsequent Paced Refractory Enable signal.

As was fully set forth in the aforereferenced Fischer application, a signal out of the operational amplifier 87 of either polarity which exceeds the pre-established threshold defined by the variable resistors 109 and 113 in FIG. 2 will cause a positive pulse to occur at the output of AND gate 218 (FIG. 3). If both flip-flops 214 and 216 are reset at the time of a naturally occurring R-wave sensed pulse, the positive transition at the output of flip-flop 216 will clock the flip-flop 226 to its set condition, thus causing the output of the flip-flop 232 to go positive for one cycle of the 10 KHz. clock. The trailing edge of this pulse clocks the flip-flop 246 in the same fashion as previously explained in connection with the reaction of the system to a Paced Refractory Enable. The remaining circuitry responds in substantially the same fashion to a sensed pulse as it did in the previous example with the exception of flip-flop 252. Because flip-flop 216 is now set, the signal through OR gate 230 maintains the flip-flop 252 in its reset state and inhibits the initiation of a Charge cycle in response to the detection of a Sensed Refractory pulse from the flip-flop 216.

Thus, it can be seen that in response to an artificial stimulating pulse from the pacer pulse generator the transistors 200, 204 and 208 of FIG. 2 will be turned on for the initial 24 millisecond portion of the paced refractory period. During this 24 millisecond interval, the voltage doubler capacitor 82 is rapidly recharged to its base level. As such, in the absence of a naturally occurring R-wave at the conclusion of the refractory period there is no appreciable voltage difference across the inputs of the operational amplifier 87 which could be construed by the system as a natural R-wave. Thus, the system of the present invention permits more reliable operation of a pacer system.

It is to be further noted that the Q output from the charge control flip-flop 252 may be connected to the gain turn down circuit as by connecting that flip-flop output to the input terminal 59 of the circuit of FIG. 2. Thus, during the period that the Charge Control flip-flop is set, the transistor 100 will be conducting thereby shorting out the feedback resistor 97, the affect of which is fully set forth in the aforereferenced Fischer application. The dynamic impedance switching of the present invention when used in conjunction with the gain turn-down feature eliminates the need for the band-pass amplifier 87 to discriminate natural R-waves from pulse generator produced pacer pulses.

While the present invention has been exemplified in connection with the description of a preferred embodiment, it is to be understood that various changes and modifications may be made to the arrangement depicted without departing from the spirit and scope of the invention. Accordingly, the scope of the present invention is to be determined from the accompanying claims.

What is claimed is:

1. In a demand type cardiac pacer system in which a resettable pulse generator means is arranged to apply artificial stimulating pulses to the heart of a patient by way of heart contacting electrodes only when naturally occurring depolarization signals are not being detected at a given rate by a sensing amplifier means also coupled to said heart contacting electrodes, apparatus for at least temporarily reducing the input impedance of said sensing amplifier means for a predetermined time period following termination of only said artificial stimulating pulses comprising:
    (a) sensing amplifier means having first and second input terminals coupled to said heart contacting electrodes and an output terminal;
    (b) a resettable pulse generator means for producing triggering pulses at a preselected rate unless said pulse generator means is reset by signals developed at said output terminal of said sensing amplifier means;
    (c) a voltage doubler circuit disposed between said pulse generator means and said heart contacting electrodes said voltage doubler circuit including a source of potential, a capacitor means and resistor means, said capacitor means and said resistor means being coupled across said source of potential, and semiconductor switching means connected to receive said triggering pulses and connected such that when triggered, the voltage of said source of potential and that on said capacitor are additively applied to said heart contacting electrodes;
    (d) further semiconductor switching means connected in shunt with said resistor means; and
    (e) control means connected to said further semiconductor switching means for rendering said further semiconductor switching means conductive for a predetermined time period only following termination of said triggering pulse.

2. Apparatus as in claim 1 wherein the input impedance of said sensing amplifier means is at least partially determined by said resistor means.

3. Apparatus as in claim 2 wherein the input impedance of said sensing amplifier means is at least 20,000 ohms when said further semiconductor switching means are non-conductive and less than 1,000 ohms when said further semiconductor switching means is conductive.

* * * * *